United States Patent [19]

Chang

[11] Patent Number: 5,466,454
[45] Date of Patent: Nov. 14, 1995

[54] METHOD AND APPARATUS FOR PRODUCING HERBAL CONCENTRATE

[76] Inventor: William Chang, 1015 S. Nogales St., Suite 120, Rowland Heights, Calif. 91748

[21] Appl. No.: 361,452

[22] Filed: Dec. 20, 1994

Related U.S. Application Data

[63] Continuation of Ser. No. 71,701, Jun. 4, 1993, abandoned.
[51] Int. Cl.$^6$ ..................................................... A61K 35/78
[52] U.S. Cl. ............................................................. 424/195.1
[58] Field of Search ........................................... 424/195.1

[56] References Cited

U.S. PATENT DOCUMENTS

| | | | |
|---|---|---|---|
| 4,230,689 | 10/1980 | Choy | 424/74 |
| 4,800,080 | 1/1989 | Grollier et al. | 424/74 |
| 5,071,653 | 12/1991 | Kakuda et al. | 424/195.1 |

*Primary Examiner*—John W. Rollins
*Attorney, Agent, or Firm*—Seldon & Scillieri

[57] ABSTRACT

The present invention provides an improved extraction process of the type in which herbs are boiled in a solvent to produce an herbal liquid that is concentrated to form an herbal extract. In a first phase of the improved process, herbs are boiled in a solvent in an extraction vessel to form an herbal liquid and an herbal vapor; the herbal vapor is drawn into a collection tank, where it is allowed to condense into an herbal condensate that is periodically re-introduced into the herbal liquid in the extraction vessel. In a second phase, a portion of the herbal liquid is drawn into a concentration vessel, where it is concentrated into herbal extract while the herbal liquid continues to boil in the extraction vessel; this second phase is repeated until there is no more herbal liquid in the extraction vessel. In a third and final phase, the last of the herbal liquid drawn into the concentration vessel from the extraction vessel is concentrated into herbal extract.

11 Claims, 1 Drawing Sheet

5,466,454

METHOD AND APPARATUS FOR PRODUCING HERBAL CONCENTRATE

This is a continuation of application Ser. No. 08/071,701 filed on Jun. 4, 1993, now abandoned.

FIELD OF THE INVENTION

This invention relates to an extraction and concentration system particularly adapted for the extraction and concentration of herbal liquids.

In recent years, research in the field of natural drugs has received more and more attention, both domestically and internationally. The United States, for example, has allotted significant funding to conduct large scale, world wide research among various medicinal plants, with an eye towards finding naturally occurring anti-cancer drugs, and the like. As used herein, the term "herb" or "medicinal herb" will be utilized to denote medicinal plants, or selected portions of such plants. The term "herbal extract" will be used to denote the extract from a medicinal plant.

In the production of herbal extract, the herb is typically boiled to form an herbal liquid. The invention herein provides an extraction and concentration process which not only avoids high temperatures and high pressures which may destroy active ingredients in medicinal herbs, but also maximizes the yield of herbal extract.

SUMMARY OF THE INVENTION

Briefly, the invention herein comprises an herbal extraction and concentration system wherein one or more types of medicinal herbs are boiled in an extraction vessel, during a first process phase, at a temperature in the preferable range of 60° to 70° C. to protect the active ingredients in the medicinal herbs from thermal destruction. The boiling process produces an herbal vapor and a herbal liquid. The herbal vapor is conducted from the extraction vessel to a collection tank for collection of the resulting herbal condensate. Herbal condensate from the collection tank is periodically fed back into the herbal liquid in the extraction vessel as the herbs are boiled.

After a time, a second process phase begins with a portion of the herbal liquid being conducted from the extraction vessel to a concentration tank. The herbal liquid conducted into the concentration tank includes condensate which has theretofore been re-introduced into the extraction vessel. During the second phase, both the concentration and extraction processes are occurring; that is, the herbs and re-introduced condensate continue to be boiled in the extraction vessel, and the herbal vapor continues to be collected as condensate for periodic reintroduction into the extraction vessel.

A third phase of the process is subsequently entered, during which the extraction process ceases, and only concentration occurs. The third phase commences with a final batch of herbal liquid from the extraction vessel being conducted to the concentration tank. Again, the herbal liquid includes herbal condensate which has been periodically fed back to the extraction vessel. The herbal liquid in the concentration tank is concentrated to complete the production process.

In accordance with one aspect of the invention, the concentration tank is constructed with a first steam jacket circumventing its sides, and a second steam jacket adjacent its bottom. The steam within the steam jackets heats the contents of the concentration tank to dehydrate the herbal liquid therein into a concentrate or paste. As described herein, steam may be independently introduced into the bottom and side steam jackets to control the points of heat application, thereby preventing burning of the concentrate, and increasing process yield.

In accordance with another aspect of the invention, the concentration tank includes a variable speed agitator which stirs the tanks contents and scrapes herbal residue from the tank's bottom to prevent burning.

Additional details concerning the invention will be apparent from the following description of the preferred embodiment, of which the drawing forms a part.

DETAILED DESCRIPTION OF THE DRAWINGS

Figure 1:
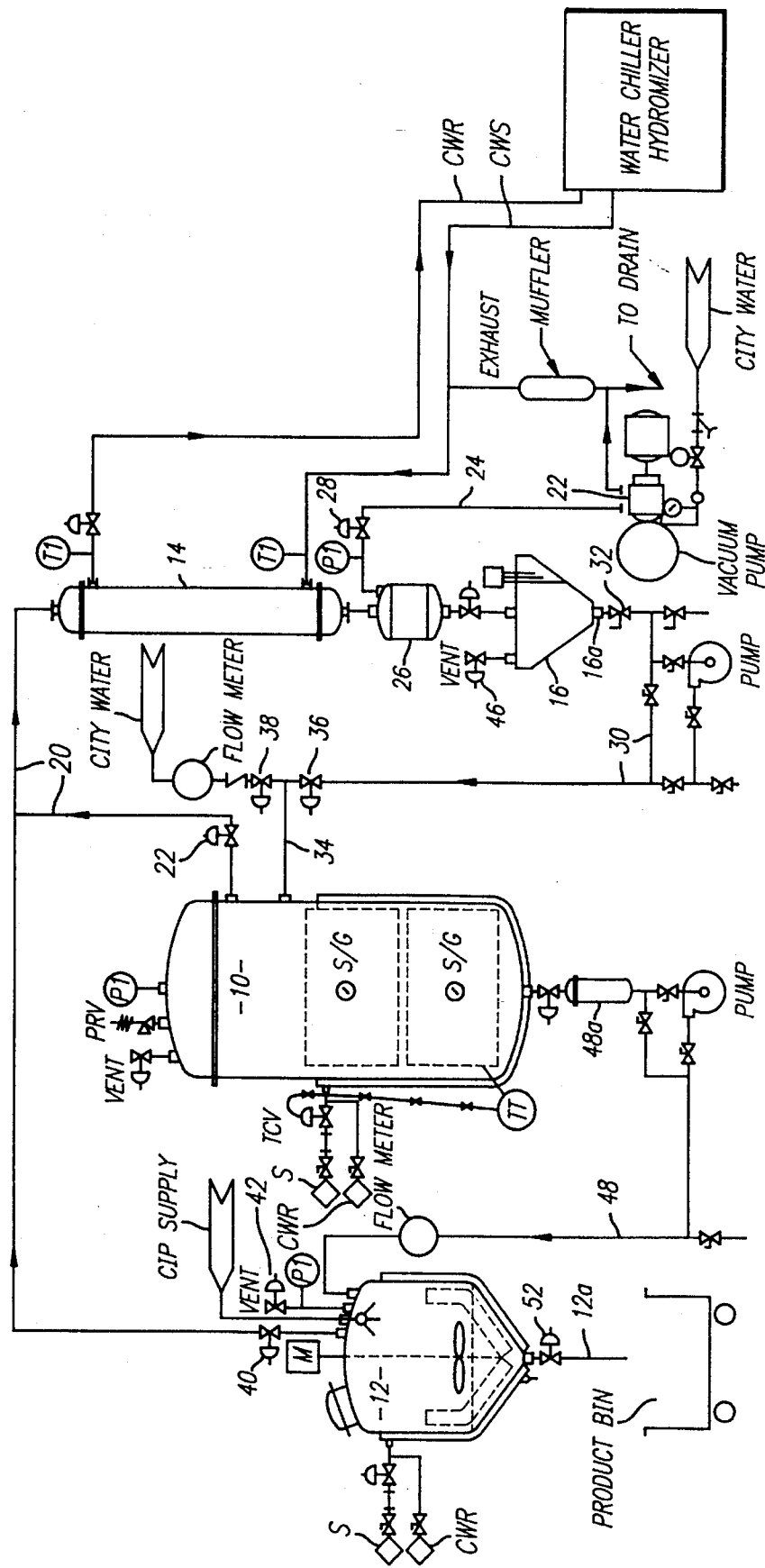

FIG. 1 is a diagram of a system for extracting and concentrating herbal liquids in accordance with the invention.

DESCRIPTION OF THE PREFERRED EMBODIMENT

FIG. 1 is a diagram of a system for extracting and concentrating medicinal herbal liquids in accordance with the invention. The system comprises an extraction vessel 10, a concentration tank 12, a condenser 14 and a collection tank 16. The interiors of the condenser 14 and collection tank 16 communicate through an intermediate 5 gallon holding tank 26 downstream from the condenser.

As will be described in detail below, herbs are boiled in the extraction vessel 10, vapor from the boiling is condensed in the condenser 14, and the resulting condensate is collected in the collection tank 16 for periodic re-introduction into the extraction vessel. After a period of time, at least a portion of the boiling herbal liquid in the extraction vessel is introduced into the concentration tank 16. An herbal concentrate is ultimately produced as a final product at the outlet 12a of the concentrator 12. Moreover, the system is microprocessor controlled to carry out the process hereinafter described at pressures and temperatures which preserve the active ingredients in the herbs.

The extraction vessel 10 is preferably a large stainless steel vessel. In practice, a 700 gallon vessel measuring 48" in diameter has been found suitable.

The extraction vessel 10 accommodates one or more baskets of the herbs which are to be boiled. Accordingly, a half-ton hoist, at least one chain basket and a 15' lift are associated with the extraction vessel, but not illustrated.

The concentration tank 12 is preferably provided shaped as a large shallow pan with a large surface area-to-height in order to maximize the rate of evaporation of its contents. In practice, a 375 gallon tank is used which is approximately 48 inches in diameter and 40 inches high. Owing to its large surface area, evaporation occurs rapidly, with rates up to approximately 30 gallons per hour.

The concentration tank employs a dual steam-jacket heating system to heat the contents in the tank to evaporate liquid therein. A first steam jacket (not illustrated) is positioned adjacent the side of the tank, and circumvents the tank along substantially the entire sidewall. The second steam jacket extends along the bottom of the tank to heat only the bottom surface. Thus, the use of both steam jackets when the tank's contents are highly liquid produces a uniform heating of the bottom and sides to maximize evaporation and speed concentration. Once the contents have been substantially concentrated, the steam jacket adjacent the tank's side can be turned off, and only the bottom steam jacket operated to minimize formation of burnt residue on the tank's side wall, thereby making the tank easier to clean between operations.

A variable speed, rotating agitator (not illustrated) is provided within the concentration tank to continuously scrape the material along the bottom of the tank, not only prevent residue at the tank's bottom from burning but also enhancing concentration time by bringing fresh material into contact with the heated bottom of the concentrator tank. During the processing of the herbal material, the rotation speed of the agitator is gradually increased from an initial speed of approximately 15 rpm to approximately 60 rpm as the tank bottom heats and the quantity of residue increases.

Having described extraction vessel and concentration tank, attention is next directed to the preferred vacuum system employed by the extraction/concentration system herein. A vacuum line 20, having an extraction valve 22, selectively couples the interiors of the extraction vessel 10 and the concentration vessel 12. Low pressure is created in the vacuum line 20 by a 1 hp, 80 gpm capacity, vacuum pump 22 that communicates with the vacuum line 20 via the interior of the condenser 14 and intermediate holding tank 26. The vacuum pump is coupled to the interior of the holding tank 26 via pump line 24. A pump line valve 28 inserted in the pump line 24 permits selective decoupling of the pump from the intermediate holding tank 26.

The interior of the collection tank 16 is selectively coupled to the interior of the extraction vessel 10 via a return line 30 having a return line valve 32. The return line 30 extends from the output end 16a of the collection tank 16 to a feed line 34 that communicates with the interior of the extraction vessel. A pair of fed line valves 36, 38 respectively permit the feed line to be coupled to the return line 30 or to a source of liquid such as a water tap.

The vacuum line 20 also communicates with the interior of the concentration tank 12 via vacuum valve 40. A vent line having a vent valve 42 selectively couples the interior of the concentration tank to ambient pressure.

In operation, a basket of herbs is loaded into the extraction vessel 10, and water is added to the vessel via feed line 34 and feedline valve 38. The herbs are then boiled at a preferred pressure of between approximately –22 and –25" Hg, and a preferred temperature of between 60° and 70° C. In practice, a boiling temperature of approximately 67° at a pressure of 18" Hg appears optimum. In this way, the system avoids the use of high temperatures and high pressures which may destroy the active ingredients in the medicinal herbs.

In this first phase of the process, the medicinally active components of the herb are extracted into the boiling water, forming an herbal liquid. At the same time, the boiling herbal liquid produces an herbal vapor which contains aromatic and volatile herbal ingredients. As now described, the herbal vapor is conducted towards a collection tank, where the resulting herbal condensate is captured and periodically reintroduced into the boiling herbal liquid within the extraction vessel.

The herbal vapor from the extraction vessel is pulled to the vapor condenser 14 via open valve 22 through vacuum line 20. The vapor condenses within the condenser 14, is collected as herbal condensate in the intermediate holding tank 26, and is held downstream therefrom in an 80 gallon stainless steel collection tank 16. The preferred condenser has a 150,000 BTU/hr capacity.

The herbal condensate in the collection tank 16 is periodically fed back to the extraction vessel to reduce the density of the liquid in the extraction tank and increase density differential. This enhances the affinity of the liquid for extracting the active herbal components from the herb(s), and thereby aids in the total extraction of the active ingredients from the herbs. In operation, the herbal condensate is fed back into the extraction vessel every 30 minutes. To accomplish the transfer, a valve 44 between the intermediate holding tank 26 and the collection tank 16 is closed, a vent valve 46 is opened to raise the pressure in the collection tank to atmospheric, and return valve 34 is opened to permit the low pressure in the extraction vessel 10 to draw the condensate into the vessel via return line 30.

In addition to carrying out the foregoing procedure every 30 minutes during the process phase, a level probe is provided in the collection tank to sense the rise of condensate level to the top portion of the tank. Upon reaching a predetermined level, the accumulated condensate thereby triggers a microprocessor signal which carries out the foregoing valve sequence to transfer condensate to the extraction vessel, and prevent overflow.

Thus, the low boiling temperature, coupled with the sealed extraction and recirculation of condensate reduces the loss of aromatic and volatile herbal ingredients. Naturally, the equipment can be used for high temperature, high pressure extraction where the herbs do not contain aromatic, volatile or other active ingredients which would be destroyed under such conditions.

After approximately two hours of boiling, the process enters a second phase wherein extraction and concentration are carried out simultaneously, reducing time required for total process. Specifically, a portion (preferably, half) of the boiling liquid in the extraction vessel is conducted into the concentration tank via a stainless steel filter assembly 48a in flowline 48. Once in the concentration vessel, the herbal liquid is concentrated by an evaporation process which includes the use of heat (via the stream jackets, as described above) and low pressure. Reduction of pressure within the concentration tank accelerates the evaporation/concentration process.

When the contents in the concentration tank become a paste, and collect along the bottom of the tank, the steam jackets along the sides are closed to prevent the paste from sticking to the sides, while the steam jackets on the bottom remain open to continue to heat the concentrate in the tank. The tank's adjustable speed agitator (described above) prevents extracted ingredients from sticking to the bottom of the concentration tank.

As indicated previously, concentration and extraction are carried out simultaneously during the second phase of the process, with the remaining contents in the extraction vessel continuing to boil, and the condensed vapor continuing to be periodically returned to the extraction vessel approximately every thirty minutes.

After the herbs have been boiled an additional two hours in the extraction vessel, the third phase of the process is initiated by conducting the remaining liquid in the extraction vessel to the concentration tank. The extraction process ceases, and only the concentration process is carried out. The condensed vapor that has been captured in the collection tank, but not yet fed back to the extraction vessel, is simply discarded, since it is essentially water. To improve process efficiency, the extraction vessel can be opened and cleaned, and the intermediate holding tank 26, collection tank 16 and interconnecting lines 20, 30 can be cleaned, for the next operation while the remaining concentration takes place. In practice, only 5 gallons of water are needed to flush the extraction vessel 10, the condenser 14, the tanks 26, 16 and the interconnecting lines 20, 30, 34.

Once concentration is completed, the concentrate is removed from the concentration tank 12 by opening a valve 52 at the tank outlet 12a. Remaining residue is then flushed out, and the tank cleaned, in preparation for the next operation.

The foregoing process is preferably microprocessor controlled, and process parameters recorded, with an Allen-Bradley SLC 150 and Partlow chart recorder. Those skilled in the art will recognize that the microprocessor utilizes sensed temperature, pressure and timing signals to open and close the heretofore described valves at the correct times and in the correct sequences.

One advantage to the use of high pressure within the extraction vessel is its retardation of foam.

Although it has been found in practice that the preferred manner for carrying out the process is to transfer one-half of the extraction vessel's contents to the concentration tank after the herbs have boiled for 2–3 hours, it will be understood that the timing and number of transfers may be varied without departing from the spirit of the invention.

Additionally, it will be understood that the extraction vessel can also be used a low pressure vacuum dehydrator/dryer (e.g. to dry concentrated paste on the racks) using the vessel's vacuum process. The vacuum eliminates wetness from the deepest layers of the herbal paste, avoiding incomplete drying which is commonly encountered when high temperature ovens are used for drying. Further, alcohol or other suitable extraction media can be used in the place of water within the extraction vessel to extract the active herbal components.

While the foregoing description includes detail which will enable those skilled in the art to practice the invention, it should be recognized that the description is illustrative in nature and that many modifications and variations will be apparent to those skilled in the art having the benefit of these teachings. It is accordingly intended that the invention herein be defined solely by the claims appended hereto and that the claims be interpreted as broadly as permitted in light of the prior art.

I claim:

1. An improved extraction process of the type including the steps of boiling herbs in a solvent to produce an herbal liquid and concentrating the herbal liquid to produce an herbal extract, the improved process comprising the steps of:

(a) boiling the herbs in a solvent in an extraction vessel at a temperature in the range of approximately 60° to 70° Centigrade to produce an herbal vapor and an herbal liquid;

(b) conducting the herbal vapor from the extraction vessel towards a collection vessel to collect a resulting herbal condensate therein;

(c) periodically adding collected herbal condensate back into the herbal liquid in the extraction vessel while continuing to boil the herbs;

(d) conducting a batch of the herbal liquid from the extraction vessel to a concentration vessel;

(e) concentrating the batch of herbal liquid to form herbal extract;

(f) continuing steps (a)–(c) while the batch of herbal liquid is being concentrated;

(g) conducting a second batch of the herbal liquid from the extraction vessel to the concentration vessel after herbal condensate has been added a second plurality of times to the extraction vessel; and (h) concentrating the second batch of herbal liquid to form herbal extract.

2. The process of claim 1 wherein the collected herbal condensate is added back into the herbal liquid in the extraction vessel approximately every 30 minutes.

3. The process of claim 1 wherein the step of periodically adding collected herbal condensate back into the herbal liquid in the extraction vessel includes further steps (c1) and (c2):

(c1) sensing the level of the herbal condensate in the collection vessel;

(c2) adding collected herbal condensate back into the herbal liquid in the extraction vessel when the herbal condensate reaches a level towards the top of the collection vessel.

4. The process of claim 1 wherein a plurality of batches of herbal liquid are conducted to the concentration vessel during the process, each of the plurality of batches being so conducted after collected herbal condensate has been added back into the herbal liquid in the extraction vessel.

5. The process of claim 1 wherein the batch of herbal liquid conducted to the concentration vessel is approximately one-half the volume of herbal liquid in the extraction vessel.

6. The process of claim 1 wherein a batch of the herbal liquid is conducted from the extraction vessel to the concentration vessel after the herbs have boiled for approximately two hours.

7. The process of claim 1 wherein a relatively subsequent batch of herbal liquid is added to the concentration vessel prior to complete concentration of the prior batch.

8. The process of claim 1 wherein the concentrating steps comprises the step of scraping the contents of the concentration tank from at least one inner surface of the tank with a variable speed agitator.

9. The process of claim 1 wherein the concentrating steps include the step of heating the sidewalls of the concentration vessel independently from the bottom of the concentration vessel.

10. The process of claim 9 including the step of deactivating the heating of the sidewalls of the concentration vessel, but maintaining the heating of the bottom of the concentration vessel, after a predetermined degree of concentration to inhibit burning of the contents of the concentration vessel.

11. An improved extraction process of the type including the steps of boiling herbs in a solvent to produce an herbal liquid and concentrating the herbal liquid to produce an herbal extract, the improved process comprising:

(a) a first phase, including the following steps:

(a1) boiling the herbs in the solvent in an extraction vessel in the temperature range of 60°–70° C., so as to produce an herbal vapor and an herbal liquid containing extracted ingredients;

(a2) periodically conducting a portion of the herbal vapor from the extraction vessel to a collection vessel;

(a3) allowing the herbal vapor to condense in the collection vessel, thereby forming an herbal condensate;

(a4) periodically feeding herbal condensate back into the extraction vessel and allowing it to mix into the herbal liquid, so as to reduce the density of the herbal liquid and to increase density differential, thereby enhancing the affinity of the herbal liquid for extracting ingredients from the herbs;
(a5) repeating steps (a1) through (a4) for a first period of time;
(b) a second phase performed at a time subsequent to the first phase, comprising the following steps:
 (b1) conducting a portion of the herbal liquid to a concentration tank;
 (b2) concentrating the herbal liquid into an herbal extract;
 (b3) simultaneously with step (b2), continuing to perform steps (a1) through (a5) on the herbs, herbal liquid, and herbal vapor remaining in the extraction vessel;
 (b4) repeating steps (b1) through (b3) for a second period of time;
(c) a third phase, including the following steps performed at a time subsequent to the second phase:
 (c1) ceasing performing steps (a1) through (a5), and (b1) through (b4);
 (c2) conducting a final batch of herbal liquid from the extraction vessel to the concentration vessel;
 (c3) concentrating the final batch of herbal liquid into herbal extract.

* * * * *